US012629283B2

(12) United States Patent
Huh et al.

(10) Patent No.: US 12,629,283 B2
(45) Date of Patent: May 19, 2026

(54) CAMERA SYSTEM AND WELDING INFORMATION PROVIDING DEVICE HAVING THE SAME

(71) Applicant: OTOS WING CO., LTD., Seoul (KR)

(72) Inventors: Moon Young Huh, Seoul (KR); Sung Won Huh, Seoul (KR)

(73) Assignee: OTOS WING CO., LTD., Seoul (KR)

( * ) Notice: Subject to any disclaimer, the term of this patent is extended or adjusted under 35 U.S.C. 154(b) by 0 days.

(21) Appl. No.: 18/798,582

(22) Filed: Aug. 8, 2024

(65) Prior Publication Data

US 2025/0099298 A1      Mar. 27, 2025

(30) Foreign Application Priority Data

Sep. 27, 2023      (KR) ........................ 10-2023-0130701

(51) Int. Cl.
| | |
|---|---|
| *A61F 9/06* | (2006.01) |
| *G02F 1/1335* | (2006.01) |
| *G06F 1/16* | (2006.01) |
| *H04N 7/18* | (2006.01) |
| *H04N 23/57* | (2023.01) |
| *H04N 23/90* | (2023.01) |
| *G02F 1/137* | (2006.01) |

(52) U.S. Cl.
CPC .......... *A61F 9/06* (2013.01); *G02F 1/133502* (2013.01); *G06F 1/163* (2013.01); *H04N 7/181* (2013.01); *H04N 23/57* (2023.01); *H04N 23/90* (2023.01); *G02F 1/137* (2013.01)

(58) Field of Classification Search
CPC .. A61F 9/06; A61F 9/065; A61F 9/067; G02F 1/133502; G02F 1/137; G06F 1/163; H04N 7/181; H04N 23/57; H04N 23/90; H04N 23/55; B23K 9/0956; G03B 11/00
USPC ............................................... 348/149; 345/8
See application file for complete search history.

(56) References Cited

U.S. PATENT DOCUMENTS

| | | | |
|---|---|---|---|
| 12,064,834 B2 * | 8/2024 | Huh ........................ | A61F 9/067 |
| 2021/0316383 A1 * | 10/2021 | Stoner .................... | H04N 23/75 |
| 2022/0023102 A1 * | 1/2022 | Huh ......................... | G02F 1/13 |
| 2022/0323257 A1 * | 10/2022 | Quijada ................... | A61F 9/06 |
| 2023/0117584 A1 * | 4/2023 | Huh ......................... | B23K 9/16 |
| | | | 345/8 |

FOREIGN PATENT DOCUMENTS

| | | |
|---|---|---|
| CN | 115867832 A | 3/2023 |
| KR | 10-2021-0034409 A | 3/2021 |
| KR | 10-2021-0034412 A | 3/2021 |
| KR | 10-2022-0112153 A | 8/2022 |

(Continued)

*Primary Examiner* — Thai Q Tran
*Assistant Examiner* — Stephen R Smith
(74) *Attorney, Agent, or Firm* — Knobbe, Martens, Olson & Bear, LLP

(57) ABSTRACT

A welding information providing device is proposed. The device may include a body provided to cover at least a portion of a worker' face and including a first region facing the worker' face and a second region located in a region opposite to the first region. The device may also include a camera unit located in the second region of the body and capturing a welding video to acquire a video frame. The device may further include a display unit located in the first region of the body and providing a video generated through the video frame.

11 Claims, 12 Drawing Sheets

(56)     References Cited

FOREIGN PATENT DOCUMENTS

| | | | | | |
|---|---|---|---|---|---|
| KR | 10-2022-0146953 | A | 11/2022 | | |
| KR | 10-2022-0147189 | A | 11/2022 | | |
| KR | 10-2022-0165238 | A | 12/2022 | | |
| KR | 10-2581930 | B1 | 9/2023 | | |
| WO | WO 2021/054753 | A2 | 3/2021 | | |
| WO | WO-2022039357 | A1 * | 2/2022 | ............. | H04N 23/60 |

* cited by examiner

CAMERA SYSTEM AND WELDING INFORMATION PROVIDING DEVICE HAVING THE SAME

CROSS-REFERENCE TO RELATED APPLICATION

This application is based on and claims priority under 35 USC § 119 to Korean Patent Application No. 10-2023-0130701, filed on Sep. 27, 2023, in the Korean Intellectual Property Office, the disclosure of which is incorporated by reference herein in its entirety.

BACKGROUND

Technical Field

The present disclosure relates to a camera system and a welding information providing device having the same.

Description of Related Technology

Workers wear protective gear to protect themselves from light and high heat generated during the welding process.

SUMMARY

The present disclosure provides a welding information providing device capable of improving welding accuracy of a worker by illustrating a welding surrounding environment to the worker.

The present disclosure also provides a welding information providing device capable of securing an accurate view during welding by preventing foreign substances from penetrating into a space providing welding information.

The present disclosure also provides a camera system and a welding information providing device that are free from a ghost phenomenon.

The technical problem to be solved by the present disclosure is not limited to the technical problem mentioned above, and other technical problems not mentioned may be clearly understood by those skilled in the art from the description below.

Additional aspects will be set forth in part in the description which follows and, in part, will be apparent from the description, or may be learned by practice of the presented embodiments of the disclosure.

According to an aspect of the inventive concept, there is provided a camera system including an imaging portion including a camera that captures a welding image to acquire a video frame and a light blocking portion located between the camera and a welding light source and including a light blocking cartridge structure that controls welding light introduced into the imaging portion.

In an embodiment of the present disclosure, the light blocking cartridge structure may include a liquid crystal panel and an anti-reflective coating layer located on at least one surface of the liquid crystal panel.

In an embodiment of the present disclosure, the light blocking cartridge structure may include an anti-reflective coating layer having a reflectivity less than 4.0%.

In an embodiment of the present disclosure, the light blocking cartridge structure may cause a virtual line perpendicular to a main surface of the light blocking cartridge structure to intersect a virtual line connecting a lens of the camera to a light source.

According to another aspect of the inventive concept, there is provided a welding information providing device including a body provided to cover at least a portion of a worker' face and including a first region facing the worker' face and a second region located in a region opposite to the first region, a camera unit located in the second region of the body and capturing a welding video to acquire a video frame, and a display unit located in the first region of the body and providing a video generated through the video frame.

In an embodiment of the present disclosure, the camera unit may include a first camera that photographs a scene other than welding to acquire a first video frame and a second camera that captures a welding video to acquire a second video frame.

In an embodiment of the present disclosure, the welding information providing device may further include an outer cover unit located in a region of the second region, wherein the outer cover unit is located in an outer region of the camera unit to protect the camera unit.

In an embodiment of the present disclosure, the outer cover unit may further include an outer cover frame and a light blocking cartridge structure located between the outer cover frame and the second camera.

In an embodiment of the present disclosure, the light blocking cartridge structure may cause a virtual line perpendicular to a main surface of the light blocking cartridge structure to intersect a virtual line connecting a lens of the second camera to a light source.

BRIEF DESCRIPTION OF THE DRAWINGS

The above and other aspects, features, and advantages of certain embodiments of the disclosure will be more apparent from the following description taken in conjunction with the accompanying drawings.

DETAILED DESCRIPTION

Figure 1:
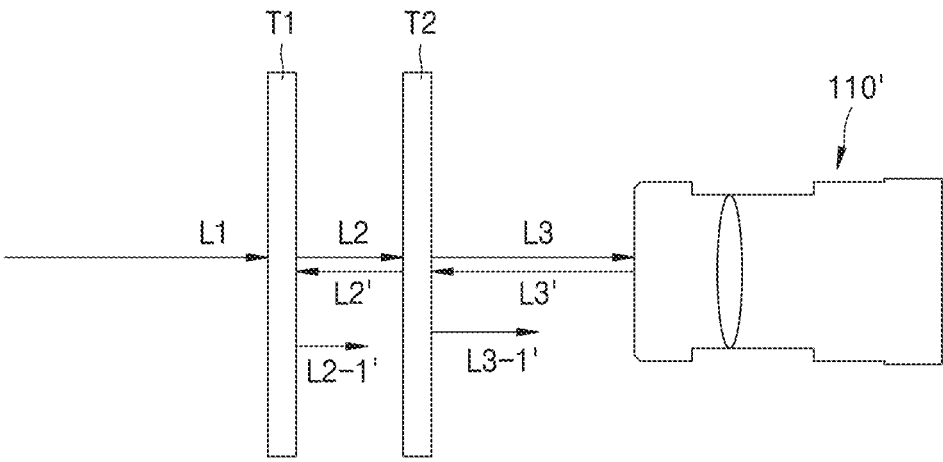
FIG. 1 is a conceptual diagram illustrating a related art camera system.

In order to check various information during a welding process, it is inconvenient to remove a protective gear and check it with the naked eye. In order to solve the problem, welding information providing devices that provide a high-definition video allowing workers to visually check even a welding surrounding environment and provide specific information on welding status information to workers have been presented.

However, welding video cameras and welding information providing devices of the related art involve a ghost phenomenon in which multiple images are captured as a strong light source of welding light is reflected from a lens or sensor surface inside a camera during the process of imaging high-temperature welding light.

Therefore, there is a need for a camera system and a welding information providing device that allows workers to safely perform welding without causing a ghost phenomenon even when high-temperature welding light is imaged.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions, such as "at least one of," when preceding a list of elements, modify the entire list of elements and do not modify the individual elements of the list.

Hereinafter, the present disclosure are described with reference to the accompanying drawings. However, the present disclosure may be implemented in various different forms and, therefore, is not limited to the embodiments described herein. In order to clearly describe the present disclosure in the drawings, parts that are not related to the description are omitted, and like reference numerals designate like elements throughout the specification.

In the drawings, the sizes of components may be exaggerated or reduced for convenience of description. For example, the size and thickness of each component shown in the drawings may be shown arbitrarily for convenience of description, and the following embodiments are not necessarily limited thereto.

Terms, such as first, second, A, B, etc. may be used to describe various components, but the components should not be limited by the terms. The above terms are used only for the purpose of distinguishing one component from another. For example, a first component may be termed a second component, and similarly, a second component may also be termed a first component without departing from the scope of the present disclosure. The term "and/or" includes any and all combinations of one or more of the associated listed items.

Throughout this specification, when it is described that a part is "connected (accessed, contact, and coupled)" to another part, the part may be "directly connected" to the other part and "indirectly connected" to the other part through a third element in between. In addition, when a part is said to "include" a certain component, this does not mean that other components are excluded but that other components may be further included, unless explicitly stated to the contrary.

The terms used herein are only used to describe specific embodiments and are not intended to limit the present disclosure. Singular expressions include plural expressions unless the context clearly dictates otherwise.

In this specification, it should be understood that terms, such as "comprise" or "have" are intended to indicate the presence of features, numbers, steps, operations, components, parts, or combinations thereof described in the specification and do not exclude in advance the possibility of presence or addition of one or more other features, numbers, steps, operations, components, parts, or combinations thereof.

Being referred to as "on" or "on" another object includes not only cases in which an object is directly on top of the other object, but also cases in which an object is present in between.

FIG. 1 is a conceptual diagram illustrating a related art camera system.

Referring to FIG. 1, the welding video cameras and welding information providing devices of the related art produce a number of ghost phenomena in which another image is captured as a strong light source of welding light is reflected from an internal lens or sensor surface in the process of imaging high temperature welding light, and therefore, there is a need for a camera system that does not cause a ghost phenomenon even when imaging high-temperature welding light, and a welding information providing device.

Meanwhile, referring back to FIG. 1, in the welding video camera systems of the related art, welding light L1 emitted from a light source passes through at least one transparent member located in a front region of a camera 110', and here, a portion of light L2 passing through a first transparent member T1 transmits L3 through a second transparent member T2, while another portion of light L2 is reflected L2' from a surface of the second transparent member T2. Here, the reflected welding light L2' is reflected again L2-1' from the first transparent member T1, and in this process, a first ghost phenomenon may occur.

In addition, a portion of the light L3 transmitting through the second transparent member T2 is again partially reflected L3' from the camera 110', and the portion L3' of the reflected welding light is again reflected L3-1' from one surface of the second transparent member T2. During this process, a second ghost phenomenon may occur.

As such, in the related art camera systems, reflection occurs several times at the interface of the transparent members T1 and T2, and as the reflected welding light are introduced into the camera 110' again, a ghost phenomenon occurs.

Figure 2:
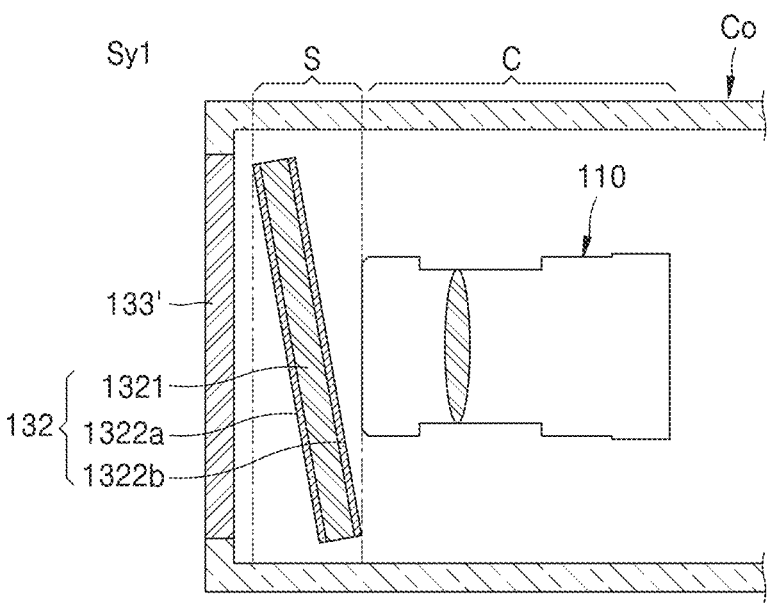
FIG. 2 is a conceptual diagram illustrating a camera system provided by an embodiment.

FIG. 2 is a conceptual diagram illustrating a camera system provided by an embodiment.

Referring to FIG. 2, an embodiment of the present disclosure provides a camera system Sy1 including an imaging portion C including a camera that captures a welding video to obtain a video frame and a light blocking portion located between the camera 110 and a welding light source and including a light blocking cartridge structure controlling welding light introduced into the imaging portion C.

The camera system according to an embodiment may be implemented in the form of a camera, a camera unit, a camera module, a camera device, etc., and these examples are not particularly limited.

Meanwhile, as in the above structure, by locating the light blocking portion S between the imaging portion C and the welding light source, a clear welding video may be captured by controlling the amount of welding light introduced into the imaging portion C.

The imaging portion C according to an embodiment of the present disclosure may further include additional components for fixing and/or operating the camera 110, such as a camera fixing unit (not referenced) for fixing the camera 110, and these components are not particularly limited.

The light blocking portion S according to an embodiment of the present disclosure may further include additional components for fixing the light blocking cartridge structure 132, such as a structure fixing portion (not referenced) for fixing the light blocking cartridge structure 132, and these components are not particularly limited.

The light blocking cartridge structure 132 according to an embodiment of the present disclosure may perform a function of blocking welding light occurring during welding work. Meanwhile, in an optional embodiment, the light blocking cartridge structure 132 may adjust a degree of light blocking based on welding light information detected through a sensor unit (not shown). Here, in another optional embodiment, the degree of light blocking may be adjusted based on welding light information detected through a separate photosensor (not shown).

The light blocking cartridge structure 132 according to an embodiment of the present disclosure may include, for example, a liquid crystal panel 1321 (LCD panel) whose degree of blackening may be adjusted depending on an alignment direction of liquid crystal. The liquid crystal panel 1321 may be implemented as various types of panels or liquid crystal panels, such as a vertical align method, a twist nematic method, in-plane switching method, etc. However, the present disclosure is not limited to the above examples, and any liquid crystal panel that may be easily selected by the ordinary person in the art should be interpreted as falling within the scope of the present disclosure.

The degree of blackening of the light blocking cartridge structure 132 according to an embodiment of the present disclosure may be automatically adjusted according to brightness of welding light. As described above, in the case of automatic adjustment according to brightness of the welding light, a sensor unit (not shown) may be used.

The sensor unit (not shown) according to an embodiment of the present disclosure may acquire welding light information by detecting the intensity of the welding light, convert the information on the intensity of the welding light included in the welding light information into a certain electrical signal, and, transmit the electrical signal to a processor (not shown), and the processor (not shown) may control the degree of blackening based on the intensity of the welding light.

The light blocking cartridge structure 132 according to an embodiment of the present disclosure may change the degree of light blocking of the liquid crystal panel 1321 in real time to correspond to the intensity of light occurring in a welding surface at a welding work site, and the imaging portion C may capture a welding video in which a certain amount of welding light is blocked by the light blocking cartridge structure 132 installed in the front portion thereof.

Referring back to FIG. 2, the camera system Sy1 according to an embodiment of the present disclosure may further include a cover portion Co located in an outer region of the light blocking cartridge structure 132 and covering the outside of the light blocking cartridge structure 132. Here, in an optional embodiment, the cover portion Co may cover both the light blocking cartridge structure 132 and the imaging portion C.

The cover portion Co according to an embodiment of the present disclosure may include a light transmitting member (not referenced) including a light transmitting material in at least a portion thereof. Welding light may pass through the light blocking cartridge structure 132 through the light transmitting member (not referenced) and, eventually, allow the imaging portion C to capture a welding video.

The light transmitting member (not referenced) according to an embodiment of the present disclosure may include a cover plate 133' located on a front side of the light blocking cartridge structure 132 and protecting the light blocking cartridge structure 132. The cover plate 133' may allow light to transmit therethrough, may include, for example, a resin material, such as polycarbonate (PC) or acrylic, and may be formed through injection molding, etc., but is not limited to the above examples.

Referring back to FIG. 2, the light blocking cartridge structure 132 according to an embodiment of the present disclosure may include a liquid crystal panel 1321 and an anti-reflective coating layer 1322a located on at least one surface of the liquid crystal panel. Here, in an optional embodiment, the anti-reflective coating layer may include a first coating layer 1322a and a second coating layer 1322b located on one surface of the liquid crystal panel and the other surface opposite to one surface.

Figure 3A:
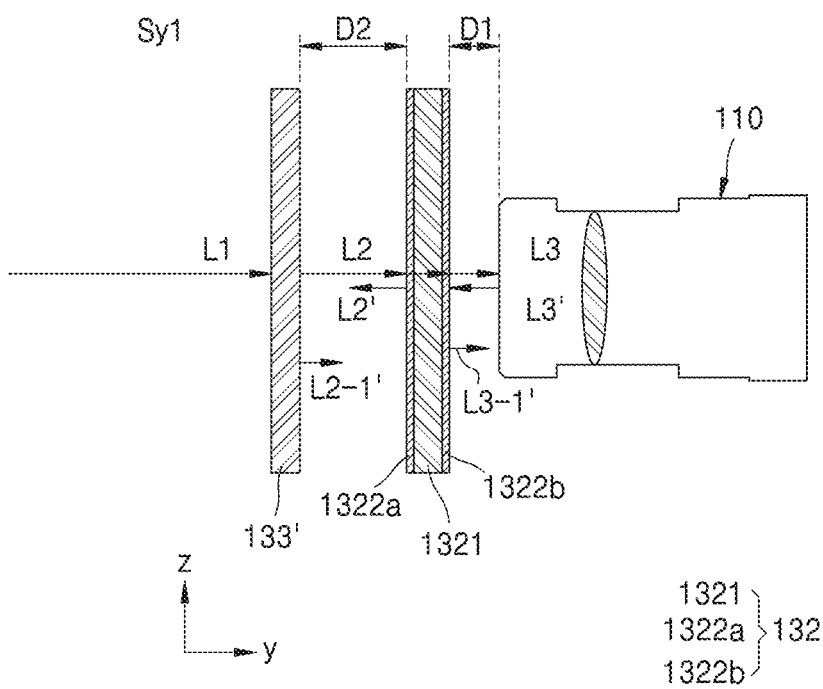
FIGS. 3A to 3C are conceptual diagrams illustrating a camera system provided by an embodiment.
Figure 3B:
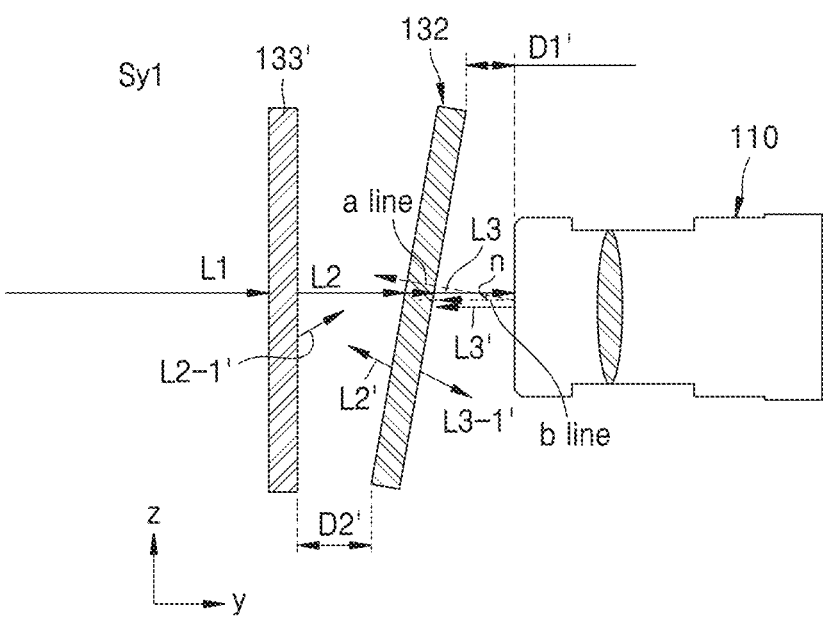
Figure 3C:
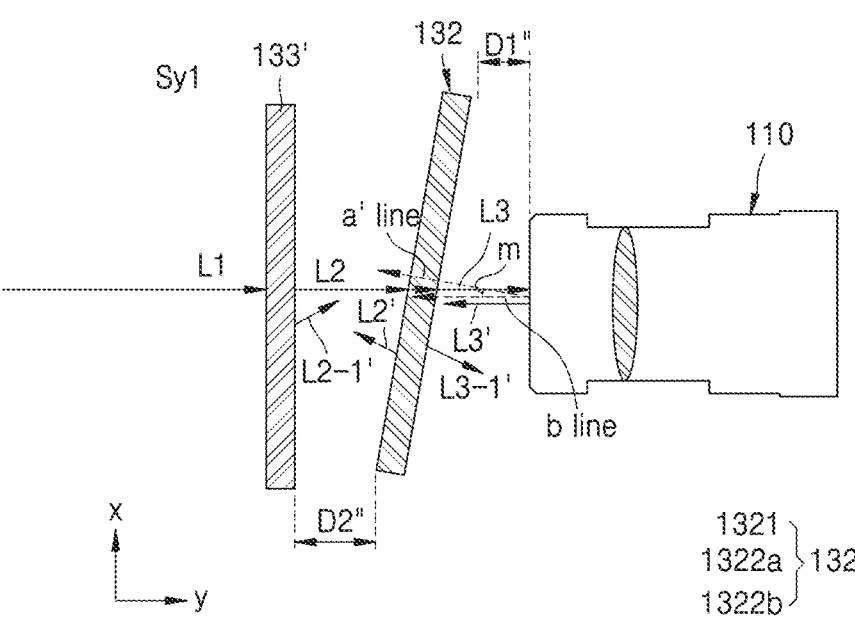

FIGS. 3A to 3C are conceptual diagrams illustrating a camera system provided by an embodiment.

Referring to FIG. 3A, when welding light passes through the cover plate 133', light reflected from the anti-reflective coating layers 1322a and 1322b located on at least one surface of the light blocking cartridge structure 132 may be reduced, thereby minimizing a ghost phenomenon.

In detail, by locating the first coating layer 1322a, when a portion of the light L2 transmitting through the cover plate 133' is reflected L2', the amount of reflected welding light L2' may be minimized, thereby minimizing the amount of welding light L2-1' that reaches the cover plate and is reflected therefrom, thereby minimizing a first ghost phenomenon.

In addition, by providing the above structure, referring to FIG. 3A, in detail, by disposing the second coating layer 1322b, when the welding light L3 transmitting through the light blocking cartridge structure 132 is reflected L3' from the camera and then reflected L3-1' from the other surface of the light blocking cartridge structure 132, the amount of reflected welding light may be minimized, thereby minimizing a second ghost phenomenon.

The anti-reflective coating layers 1322a and 1322b according to an embodiment of the present disclosure may be formed by a method of forming a film by applying a coating layer and drying and/or curing the coating layer, such as vacuum deposition, sputtering, and/or wet coating. However, the present disclosure is not limited to the above forming and/or coating methods, and all forming and/or coating methods of the anti-reflective coating layer that may be easily selected by a person skilled in the art should be construed as falling within the scope of the present disclosure.

The anti-reflective coating layers 1322a and 1322b according to an embodiment of the present disclosure may be formed and/or coated with, for example, magnesium fluoride (MgF2), silicon (Si), and silicon dioxide (SiO$_2$), etc. but are not limited to the above materials, and any anti-reflective coating layer material that may be easily selected by a person skilled in the art should be construed as falling within the scope of the present disclosure.

If reflectivity of the anti-reflective coating layers 1322a and 1322b according to an embodiment of the present disclosure is too high, the amount of welding light transmitting through the light blocking cartridge structure 132 may be insufficient, thereby reducing the clarity of a video, whereas if the reflectivity of the anti-reflective coating layers 1322a and 1322b is too low, the efficiency of the anti-reflective coating layers 1322a and 1322b may decrease and a ghost phenomenon is not eliminated, and thus, the reflectivity may be adjusted to be less than 4%, less than 3.5%, less than 3.0% in another example, and 1.0% or less in another example.

A refractive index of the anti-reflective coating layers 1322*a* and 1322*b* according to an embodiment of the present disclosure may be 1.3 to 1.36.

The anti-reflective coating layers 1322*a* and 1322*b* according to an embodiment of the present disclosure may include a single layer or a plurality of layers, and at least two of the plurality of layers may have different refractive indices.

Referring back to FIG. 3B, the light blocking cartridge structure 132 according to an embodiment of the present disclosure may cause a virtual 1-1-th line (line a) perpendicular to a main surface of the light blocking cartridge structure 132 to intersect a virtual second line (line b) connecting the camera to a light source. Here, the line b may be, for example, an optical axis.

In this specification, "main surface" may refer to the largest surface of a film, film structure, thin film, membrane, layer, or structure having a large surface similar thereto.

In this specification, "light source" may refer to an object or tool that emits light and may refer to, for example, a place where welding imaged by a worker takes place, or an object that is welded and generates welding light.

With the line b and line an intersecting each other as in the above structure, when the welding light L2' reflected from one surface of the light blocking cartridge structure 132 reaches the cover plate 133' and is reflected L2-1', the reflected light L2-1' is not directed to the camera 110, and accordingly, the aforementioned first ghost phenomenon may be minimized (see FIG. 3B).

With the line b and line an intersecting each other as in the above structure, even when the welding light L3' reflected from a region of the camera 110 reaches the light blocking cartridge structure 132 and is reflected L3-1', the reflected welding light L3-1' is not directed toward the camera 110, a second ghost phenomenon may also be minimized (see FIG. 3B).

Referring back to FIG. 3B, according to an embodiment, the angle n formed between line b and line a may be set to range from 0 degrees to 10 degrees. Through the above structure, the ghost phenomenon may be minimized even when welding light is reflected from the cover plate 133' and/or the light blocking cartridge structure 132.

FIG. 3B is a diagram illustrating a movement path of welding light in a y-z direction representing a lateral direction of the camera 110, and FIG. 3C is a diagram illustrating a movement path of welding light in a y-x direction representing a vertical direction of the camera 110.

Referring to FIG. 3C, the light blocking cartridge structure 132 according to an embodiment may cause a virtual 1-2-th line (line a') perpendicular to the main surface of the light blocking cartridge structure 132 to intersect a virtual second line (line b) connecting the camera 110 to the light source W. Here, the line a, the line a', and the line b may each intersect each other.

Meanwhile, an angle m formed by the line a' and the line b may be determined independently of an angle n formed by the line a and the line b.

As with the above structure, by varying the angle between the light blocking cartridge structure 132 and the camera 110 and/or the cover plate 133', the camera system capable of minimizing a ghost phenomenon by considering a position in which the camera system is driven, a scale of a welding environment, etc. may be provided.

Although not shown in the drawings, the camera system according to an embodiment of the present disclosure may further include a controller (not shown) that controls the angle n formed by the line a and the line b and/or the angle m formed by the line a' and the line b. In the camera system, a path through which welding light is introduced may vary depending on a location in which the imaging portion is located. By having the above structure, the effect of preventing a ghost phenomenon depending on the location of use may be provided.

In the camera system according to an embodiment of the present disclosure, the light blocking cartridge structure 132 may further include a driving unit (not shown) that adjusts the arrangement angle of the light blocking cartridge structure 132 in a portion of the light blocking cartridge structure 132. For example, a driving range of at least one of the angle n and the angle m may be driven to a range of at least 3 degrees or more.

Meanwhile, such a controller and driving unit are not particularly limited, and a component which may be configured to control the arrangement surface and/or arrangement angle of the panel and/or thin plate and which may be easily selected by the skilled person in the art of the present disclosure may be construed as falling within the scope of the present disclosure.

Referring back to FIG. 3A, in an embodiment, a distance D1 between a region of the light blocking cartridge structure 132 and the camera 110 may be less than a distance D2 between a region of the light blocking cartridge structure 132 and the cover plate 133'. Referring to FIG. 3A, in an optional embodiment, D1 may refer to a distance between the second coating layer 1322*b* and the camera 110. In another optional embodiment, D1 may refer to a distance between the second coating layer 1322*b* and a lens of the camera 110.

In addition, although not shown in the drawing, in an optional embodiment, a region of the light blocking cartridge structure 132 may be brought into contact or close contact with a portion of the camera 110, and in another optional embodiment, a region of the light blocking cartridge structure 132 may be brought into contact or close contact with a portion of the lens of the camera 110. As in the above structure, when D1 is smaller, the amount of welding light L3' reflected from the camera 110 may be minimized, and through this, a ghost phenomenon may be minimized.

Referring back to FIG. 3B, in an embodiment, a minimum distance D1' between a region of the light blocking cartridge structure 132 and the camera 110 may be less than a minimum distance D2' between a region of the light blocking cartridge structure 132 and the cover plate 133'.

In addition, although not shown in the drawings, in an optional embodiment, a region of the light blocking cartridge structure 132 may be brought into contact or close contact with at least a portion of the camera 110. As in the above structure, when D1' is smaller, the amount of welding light L3' reflected from the camera 110 may be minimized, and through this, a ghost phenomenon may be suppressed.

Referring back to FIG. 3C, in an embodiment, a minimum distance D1" between a region of the light blocking cartridge structure 132 and the camera 110 may be less than a minimum distance D2" between a region of the light blocking cartridge structure 132 and the cover plate 133'.

In addition, although not shown in the drawings, in an optional embodiment, a region of the light blocking cartridge structure 132 may be brought into contact or close contact with at least a portion of the camera 110. As with the above structure, when D1" is smaller, the amount of welding light L3' reflected from the camera 110 may be minimized, thereby suppressing a ghost phenomenon.

Figure 4:
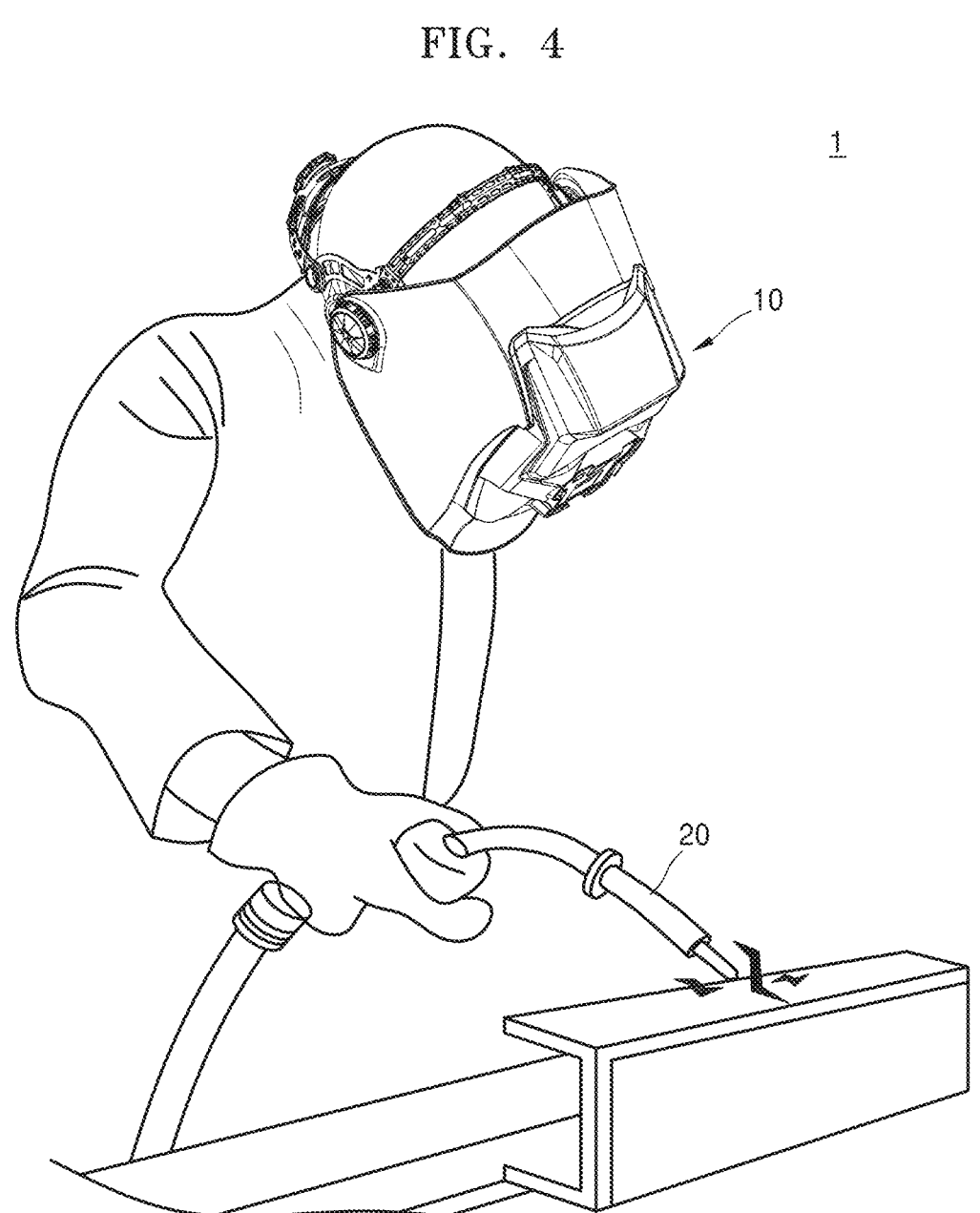
FIG. 4 is a diagram illustrating a structure of a welding system according to an embodiment of the present disclosure.
Figure 5:
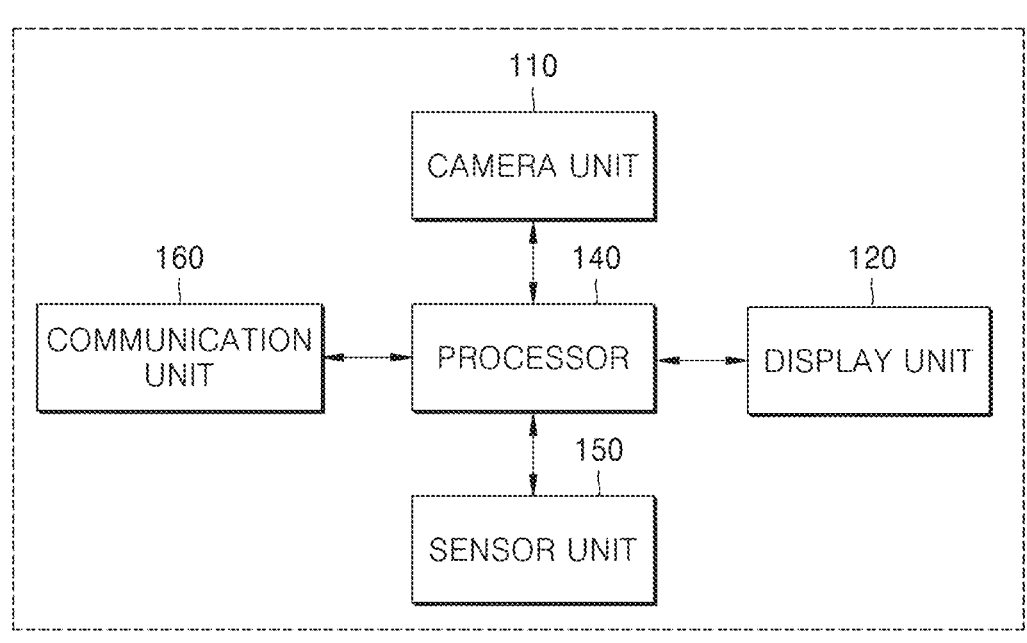
FIG. 5 is a simplified block diagram illustrating components of a welding system according to an embodiment of the present disclosure.

FIG. 4 is a diagram illustrating a structure of a welding system according to an embodiment of the present disclosure. FIG. 5 is a simplified block diagram illustrating components of a welding system according to an embodiment of the present disclosure.

Referring to FIG. 4, a welding system 1 according to an embodiment of the present disclosure may include a welding information providing device 10 and a welding torch 20.

The welding information providing device 10 and the welding torch 20 may be connected to each other through a communication network and may transmit and receive data. The welding information providing device 10 and the welding torch 20 may match and operate in a one-to-one manner, but are not limited thereto, and various modifications may be made, such that they match and operate in a one-to-many manner. In other words, n welding torches 20 may be connected to one welding information providing device 10, and one welding torch 20 may be connected to n welding information providing devices 10.

In an optional embodiment, the welding information providing device 10 and the welding torch 20 may exchange data by communicating with a separate server (not shown).

The welding information providing device 10 according to an embodiment of the present disclosure may provide information on a welding situation to the worker. In detail, the welding information providing device 10 may acquire a welding video frame and/or a welding image using at least one camera mounted on the welding information providing device 10.

Based on this, a composite video may be generated and displayed to the worker. The welding information providing device 10 according to an embodiment may generate a composite video using high dynamic range (HDR) technology, and display and provide a high-definition composite video to the worker. Here, the worker may be able to visually check a shape of a welding bead and information on the surrounding environment other than a portion adjacent to welding light through the high-definition composite video.

Meanwhile, in the case of the welding information providing devices 10 presented in the related art, in the process of imaging high-temperature welding light, a ghost phenomenon occurs in which another image is captured as a strong light source of welding light is reflected from an internal lens or a sensor surface, resultantly making it difficult for the worker to perform work.

Referring to FIG. 5, the welding system 1 according to an embodiment of the present disclosure may include the camera unit 110 that acquires a video frame and a display unit 120 that provides a video to the worker using the obtained video frame, and may include a processor 140 that controls the camera unit 110 and the display unit 120. The welding system 1 according to an embodiment is described in more detail below.

Figure 6:
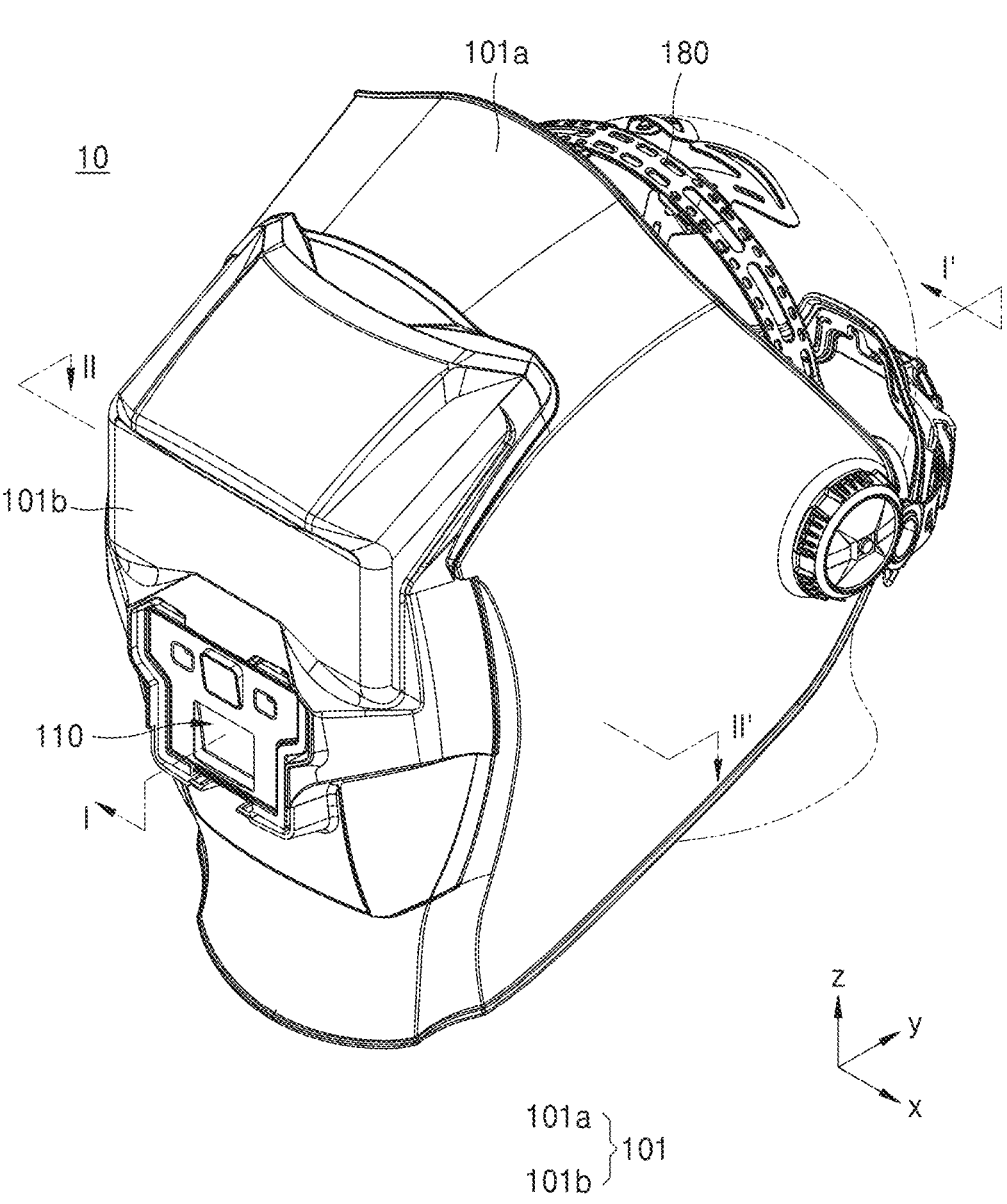
FIG. 6 is a perspective view of a welding information providing device according to an embodiment of the present disclosure.
Figure 7:
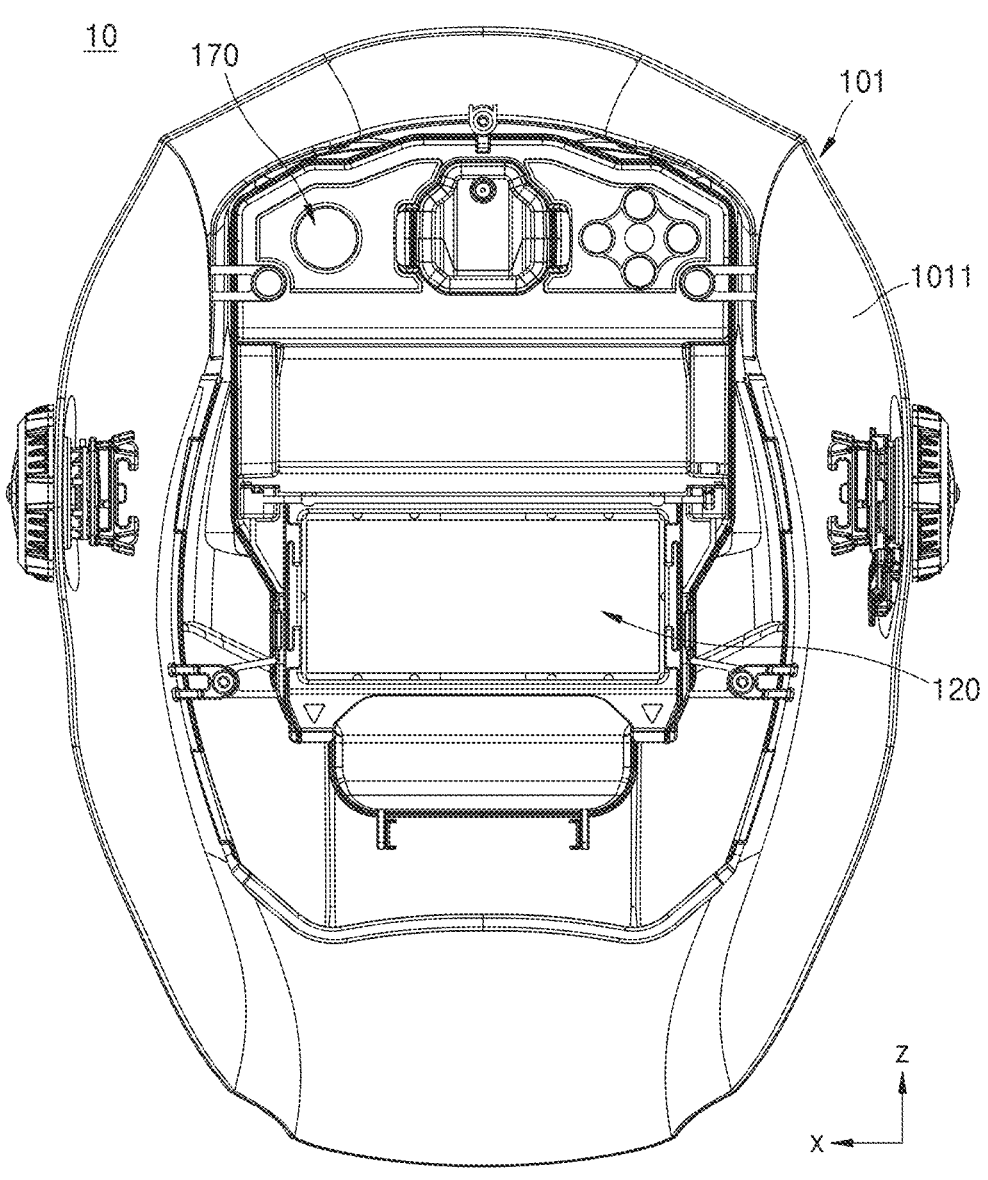
FIG. 7 is a rear view of a welding information providing device according to an embodiment of the present disclosure.

FIG. 6 is a perspective view of a welding information providing device according to an embodiment of the present disclosure. FIG. 7 is a rear view of a welding information providing device according to an embodiment of the present disclosure.

Referring to FIGS. 6 and 7, in order to solve the above technical problem, an embodiment of the present disclosure includes a body 101 provided to cover at least a portion of the worker' face, the camera unit 110 located in a region of the body 101 and acquiring a video frame by imaging a welding scene, and the welding information providing device 10 located in another region of the body 101 and including the display unit 120 that provides a video generated through the video frame.

Here, the body 101 may include a first region 1011 facing the worker' face and a second region 1012 located in a region opposite to the first region 1011, the camera unit 110 may be located in the second region, and the display unit 120 may be located in the first region 1011.

The body 101 according to an embodiment of the present disclosure may be intended to protect the face of the worker performing welding work and may be provided so that the worker may wear it. The body 101 may be formed of a material having a certain strength, such as reinforced plastic. However, without being limited thereto, any material that is resistant to elements, such as sparks that may occur during welding work, may be used in a variety of ways.

The body 101 according to an embodiment of the present disclosure may be fixed to the worker' head through a head fixing portion 180 provided on the inside of the body 101. In detail, the head fixing portion 180 may be rotatably connected to the body 101, and as the head fixing portion 180 is in contact with the worker' head and is fixed in position, the body 101 connected to the head fixing portion 180 may be stably fixed.

The head fixing portion 180 according to an embodiment of the present disclosure may be located in the first region 1011 of the body 101 and may be connected to the body 101. The worker may bring the head fixing portion 180 into contact with the head of the worker, and accordingly, the position of the welding information providing device 10 may be stably fixed.

The head fixing portion 180 according to an embodiment of the present disclosure may include an adjusting portion (not referenced) that may adjust a length of an inner circumference of the head fixing portion 180 according to the size of the worker' head.

The worker may grip the adjusting portion (not referenced) and adjust the circumference of the head fixing portion 180 by rotating the adjusting portion clockwise or counterclockwise, so that the head fixing portion 180 and the body 101 connected to the head fixing portion 180 may be stably fixed in position on an outer side of the worker's head.

Referring to FIG. 6, both sides of the head fixing portion 180 according to an embodiment of the present disclosure may be connected to the body 101. Both sides of the head fixing portion 180 may be rotatably connected to the body 101, and in a state in which the head fixing portion 180 is fixed in position on the worker's head, the worker may rotate the body 101 to secure a field of view of the worker regarding an external environment.

A rotating portion according to an embodiment of the present disclosure adjusts the length of circumference of the head fixing portion 180 by rotation, but without being limited thereto, various modifications may be made within the technical concept in which the head fixing portion 180 is in close contact with the worker' head, such as adjusting the length of the circumference of the head fixing portion 180 slidably or by a button.

The head fixing portion 180 according to an embodiment of the present disclosure may include a plurality of ribs (not shown) like a headgear, and components including soft materials, such as a fiber member (not shown) or a cushion member (not shown) may be further provided in at least a partial region on an inner side in direct contact with the head of the worker who perform welding work.

Referring to FIG. 6, the body 101 according to an embodiment of the present disclosure may include an outer frame portion 101*a* forming an outer circumference of the body 101 and an inner body portion 101*b* in which the camera unit 110, the display unit 120, an outer cover unit 130, an inner cover unit (not referenced), etc., which are to be described below.

On the body 101 according to an embodiment of the present disclosure, the camera unit 110, the display unit 120, the processor 140, a sensor unit 150, the outer cover unit 130, the head fixing portion 180, a communication unit 160, etc. may be located, and the body 101 may protect the worker from sparks, heat, etc. that occur during welding work.

The camera unit 110 according to an embodiment of the present disclosure may be mounted on the body 101, may capture and acquire a welding video frame and/or welding image for welding work, and may include a camera.

The camera unit 110 according to an embodiment of the present disclosure may be located in the second region 1012 of the body 101 and may include at least one camera that acquires a welding video frame and/or a welding image. Meanwhile, the camera unit 110 according to an embodiment may include a first camera 1101 that acquires a first video frame by imaging a scene other than welding and a second camera 1102 that acquires a second video frame by imaging a welding scene.

In this specification, a "scene other than welding" may refer to a scene in which welding is in progress, and a "video other than welding" may refer to all videos excluding a video obtained by imaging the scene other than welding or a welding video obtained by imaging a welding scene, for example, may refer to a video excluding a welding video and may include a pre-welding video and/or post-welding video.

In this specification, "welding video" may include a video including a video frame in which welding is in progress.

The first camera 1101 according to an embodiment of the present disclosure may be located on a front portion of the body 101 corresponding to the worker' field of view. According to an optional embodiment, the first camera 1101 may be located near the worker' field of view. Accordingly, the welding information providing device 10 may acquire a video image similar to that when viewing directly without using the welding information providing device 10, while performing work other than welding work, and may provide more accurate information to the worker.

The first camera 1101 according to an embodiment of the present disclosure includes a single camera and may acquire a welding video frame for welding work, but the present disclosure is not limited thereto. In an optional embodiment, the first camera 1101 may include two cameras arranged in positions corresponding to the worker' left and right eyes, respectively.

The second camera 1102 according to an embodiment of the present disclosure may acquire a second video frame by imaging a welding scene. Here, the second camera 1102 may be located in a front portion of the body 101 corresponding to the worker' field of view. Accordingly, the welding information providing device 10 may acquire a welding image similar to that when viewing directly without using the welding information providing device 10, while performing work other than welding work, and may provide more accurate welding information to the worker.

According to an embodiment of the present disclosure, the first camera 1101 and the second camera 1102 may be arranged up and down when the worker wears the welding information providing device 10. Here, a middle region of a virtual line connecting the centers of the first camera 1101 and the second camera 1102 may be located in the front portion corresponding to the worker' field of view. As in the above structure, by arranging the first camera 1101 and the second camera 1102 in positions corresponding to the worker' field of view, a welding image similar to that when viewing directly without using the welding information providing device 10 may be acquired, and more accurate welding information may be provided to the worker.

The camera unit 110 according to an embodiment of the present disclosure may further include a thermal imaging camera. The welding information providing device 10 may acquire a specific temperature video of welding work by synthesizing a thermal image video acquired through the thermal imaging camera with a video of welding work.

The camera unit 110 according to an embodiment of the present disclosure may include a camera that receives a control command from the processor 140 to be described below and changes settings, such as a shutter speed, ISO sensitivity, and gain in response to the control command to perform a welding work phenomenon.

Figure 8A:
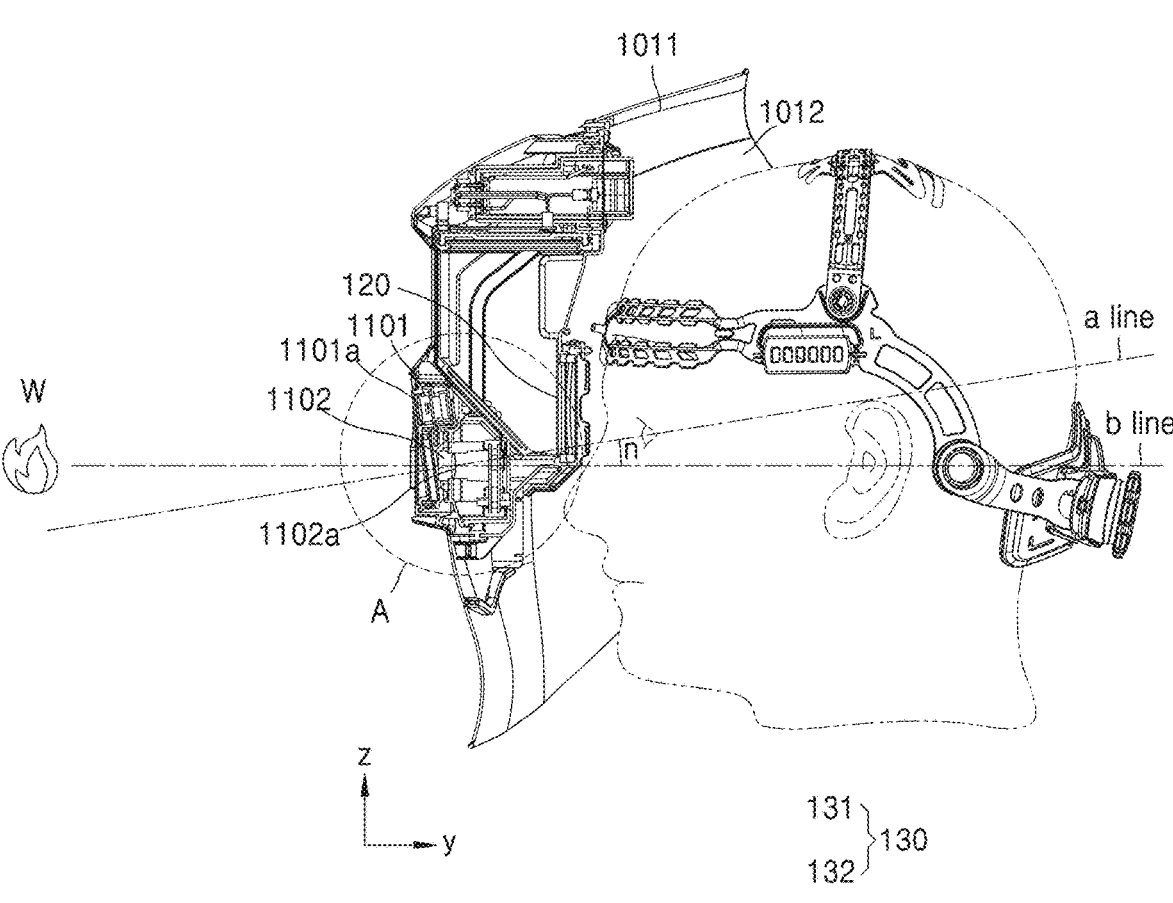
FIG. 8A is a cross-sectional view taken along line I-I' of FIG. 6.
Figure 8B:
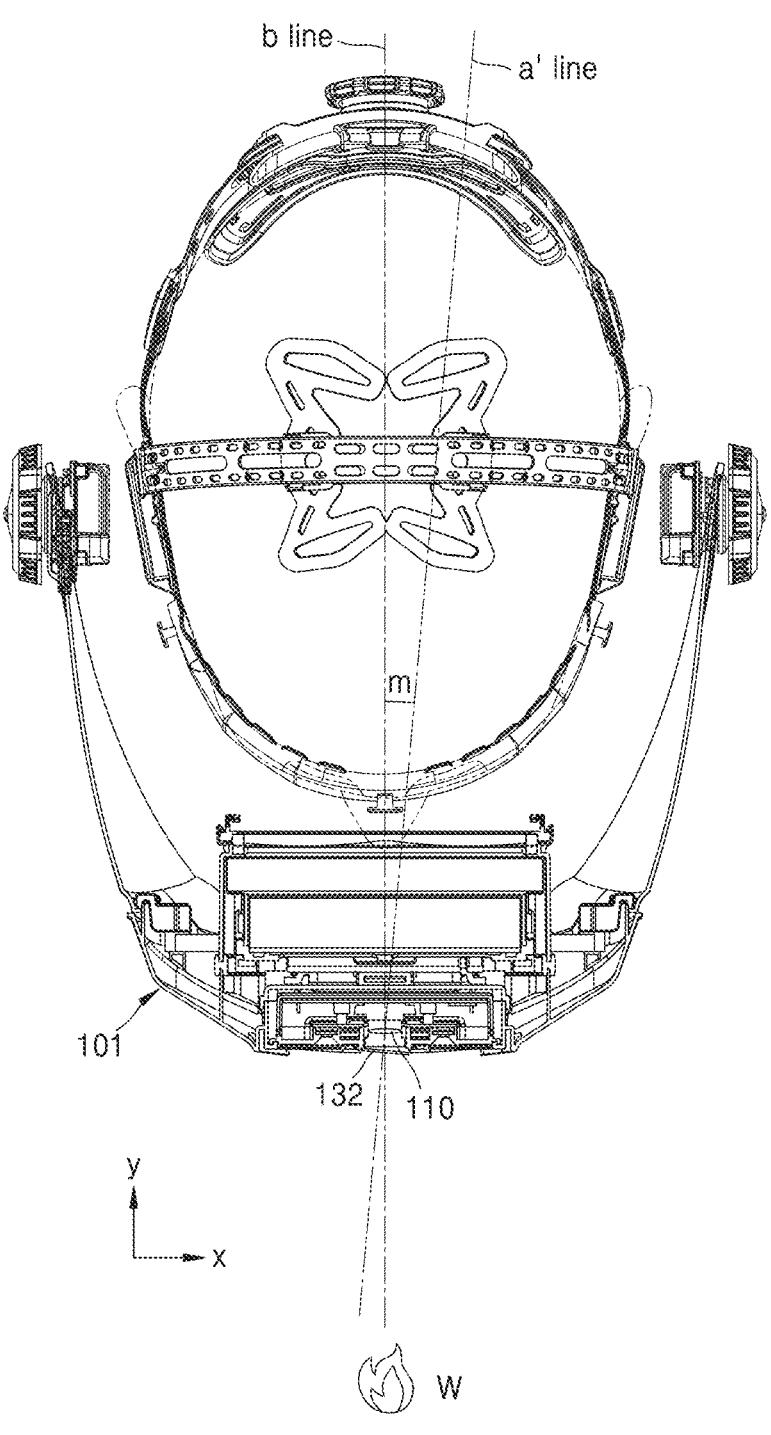
FIG. 8B is a cross-sectional view taken along line II-II' of FIG. 6.
Figure 9:
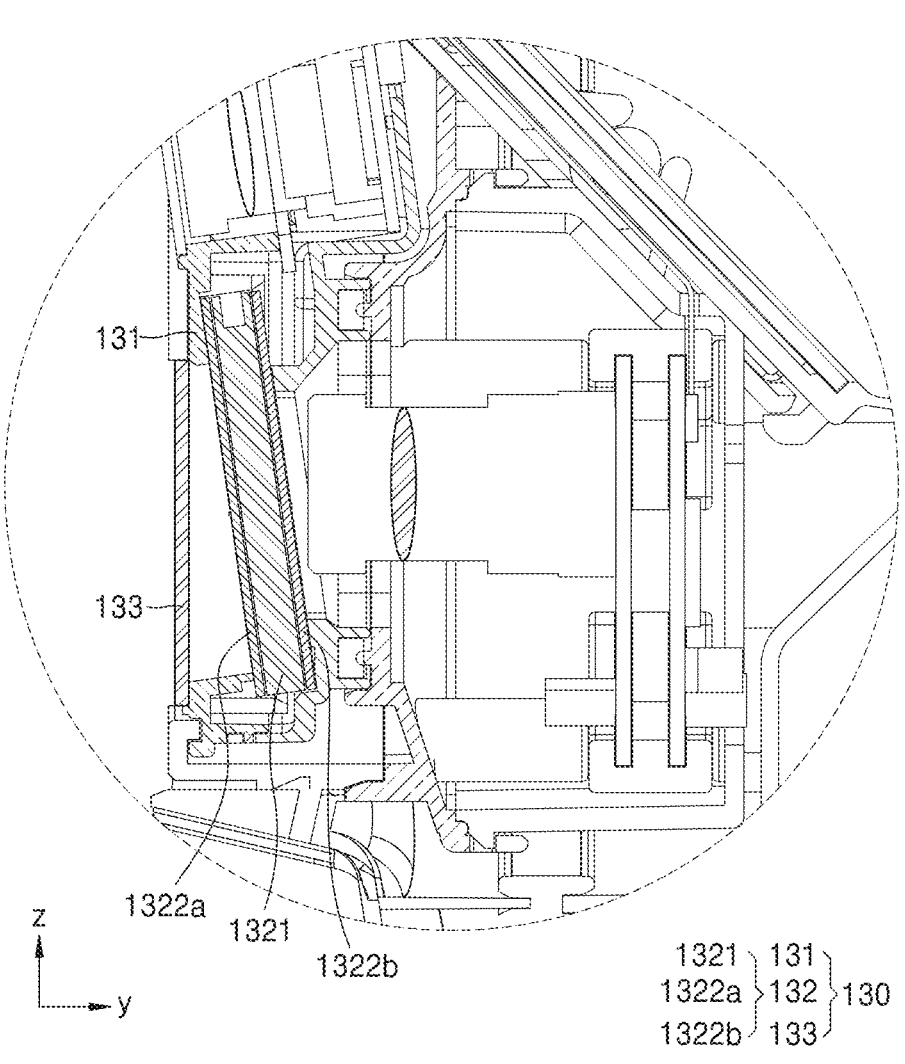
FIG. 9 is an enlarged view of region A of FIG. 8A provided by an embodiment.

FIG. 8A is a cross-sectional view taken along line I-I' of FIG. 6. FIG. 8B is a cross-sectional view taken along line II-II' of FIG. 6. FIG. 9 is an enlarged view of region A of FIG. 8A provided by an embodiment.

Referring to FIGS. 8A and 9, the welding information providing device 10 according to an embodiment of the present disclosure may further include the outer cover unit 130 located in a region of the second region 1012. The outer cover unit 130 may cover at least a portion of the camera unit 110 from the outside of the camera unit 110, and through this, the camera unit 110 may be protected by the outer cover unit 130.

Referring back to FIG. 8A, the outer cover unit 130 according to an embodiment of the present disclosure may include an outer cover frame 131, an outer cover plate 133, and the light blocking cartridge structure 132.

The outer cover frame 131 according to an embodiment of the present disclosure may perform a function of connecting the outer cover unit 130 to the body 101. Accordingly, the outer cover unit 130 may be stably located in and/or fixed to the body 101.

The outer cover plate 133 according to an embodiment of the present disclosure may be located on a front side of the light blocking cartridge structure 132, to be described below, and may protect the light blocking cartridge structure 132. The outer cover plate 133 may include a material that allows light to pass therethrough, for example, a transparent material. The outer cover plate 133 may include a resin material, such as polycarbonate (PC) or acrylic, and may be molded by injection molding, but is not limited to the above example.

A detailed description of the light blocking cartridge structure 132, the relationship between the light blocking cartridge structure 132 and the cover plate 133' and/or the outer cover plate 133, and the relationship between the light blocking cartridge structure 132 and the camera 110 according to an embodiment of the present disclosure is replaced with the description in the previous embodiments.

Referring back to FIGS. 3A to 3C, the welding information providing device 10 according to an embodiment of the present disclosure may further include a light blocking cartridge structure 132 controller (not shown) that controls the angle n formed by the line a and the line b and/or the angle m formed by the line a' and the line b. Here, the light blocking cartridge structure 132 may further include a driving unit (not shown) that adjusts the arrangement angle of the light blocking cartridge structure 132 in a portion thereof. Here, for example, a driving range of at least one of the angle n and the angle m may be driven to a range of at least 3 degrees or more.

Through the above structure, when a ghost phenomenon occurs depending on the welding environment, etc. while using the welding information providing device 10, the worker may remove the ghost phenomenon by adjusting the angle of the light blocking cartridge structure 132 according to the situation.

Meanwhile, the controller and driving unit are not particularly limited, and a component which may be configured to control the arrangement surface and/or arrangement angle of the panel and/or thin plate and which may be easily selected by the skilled person in the art of the present disclosure may be construed as falling within the scope of the present disclosure.

The welding information providing device 10 according to an embodiment of the present disclosure may provide a function of displaying welding information in a preferred color (e.g., green, blue) using RGB.

The welding information providing device 10 according to an embodiment of the present disclosure may provide a magnifying glass power correction function (e.g., screen enlargement and reduction).

Referring back to FIG. 5, the processor 140 according to an embodiment of the present disclosure may be electrically connected to the communication unit 160, the display unit 120, the sensor unit 150, and/or the camera unit 110 and may control driving of the welding information providing device 10 by transmitting and receiving electrical signals therebetween. For example, the processor 140 may control the display unit 120 to display a welding video generated based on a welding video frame and/or a welding image.

The processor 140 according to an embodiment of the present disclosure may generate a high-quality composite video by synthesizing welding video frames received through the camera unit 110. The processor 140 may cause the camera unit 110 to set different imaging conditions for each frame and synthesize frames acquired in time order in parallel to acquire a composite video. In an optional embodiment, the processor 140 may control the camera unit 110 to capture images by changing a shutter speed, ISO sensitivity, and gain of the camera of the camera unit 110.

The processor 140 may set different imaging conditions depending on conditions, such as sensed welding light at a welding site, ambient light, and the degree of movement of the welding torch 20. In detail, the processor 140 may set imaging conditions so that the ISO sensitivity and gain decrease as the welding light and/or ambient light at the welding site increases. If the movement of the welding torch 20 and/or work speed is detected to be fast, imaging conditions may be set to increase the shutter speed.

The processor 140 according to an embodiment of the present disclosure may synthesize videos of a preset number of frames in parallel. Here, each video within the preset frame may have been captured under different imaging conditions.

When there are two or more cameras in the camera unit 110, the processor 140 according to an embodiment of the present disclosure may control imaging setting conditions of each camera to be different and control the two cameras to perform imaging. Even in this case, the processor 140 may synthesize videos of a preset number of frames in parallel.

The processor 140 according to an embodiment of the present disclosure may control the overall operation of the welding information providing device 10 using various programs stored in memory (not shown).

For example, the processor 140 may include a CPU, RAM, ROM, and a system bus. Here, the ROM may be a component in which a set of instructions for system booting is stored, and the CPU may copy an operating system (OS) stored in the memory of the welding information providing device 10 to RAM according to the instructions stored in the ROM and executes the O/S to boot the system. Once booting is complete, the CPU may copy various applications stored in the memory to RAM and execute them to perform various operations. Although the processor 140 is described above as including only one CPU, the processor 140 may be implemented with multiple CPUs (or DSP, SoC, etc.).

The processor 140 according to an embodiment of the present disclosure may be implemented as a digital signal processor (DSP), a microprocessor, and/or a time controller that processes digital signals. However, without being limited to the above examples, the processor 140 may include one or more of a central processing unit (CPU), a micro controller unit (MCU), a micro processing unit (MPU), a controller, an application processor, a communication processor, an ARM processor or may be defined in by the corresponding term.

The processor 140 according to an embodiment of the present disclosure may be implemented as a system on chip (SoC) with a built-in processing algorithm or large scale integration (LSI) or may be implemented in the form of a field programmable gate array (FPGA).

Referring back to FIG. 5, the communication unit 160 according to an embodiment of the present disclosure may receive welding information from the welding torch 20 and transmit a command to control the welding torch 20.

According to an embodiment of the present disclosure, the communication unit 160 may transmit a composite image to an external device other than the welding torch 20. Here, the external device may include various devices including communication modules, such as smartphones and computers of workers/third parties.

The communication unit 160 according to an embodiment of the present disclosure may communicate with various types of external devices according to various types of communication methods. The communication unit 160 may include at least one of a Wi-Fi chip, a Bluetooth chip, a wireless communication chip, and an NFC chip.

In particular, when using a Wi-Fi chip or a Bluetooth chip, various connection information, such as SSID and session key, may be first transmitted and/or received, and various information may be transmitted and/or received after establishing a communication connection using the same.

A wireless communication chip may refer to a chip that performs communication according to various communication standards, such as IEEE, Zigbee, 3rd Generation (3G), 3rd Generation Partnership Project (3GPP), and Long Term Evolution (LTE).

A near field communication (NFC) chip may refer to a chip that operates in the NFC manner using a 13.56 MHz band among various RF-ID frequency bands, such as 135 kHz, 13.56 MHz, 433 MHz, 860 to 960 MHz, 2.45 GHz, etc.

The communication unit 160 according to an embodiment of the present disclosure may transmit and receive data to and from the welding information providing device 10. The communication unit 160 may include a module capable of short-range wireless communication (e.g. Bluetooth, Wifi, Wifi-Direct) or long-distance wireless communication (e.g. 3G, high speed downlink packet access (HSDPA), or LTE).

Referring back to FIG. 5, the sensor unit 150 according to an embodiment of the present disclosure may include a plurality of sensor modules configured to detect various information on the welding site and acquire welding information. The welding information may include a welding temperature, a welding direction, a welding slope, and a welding speed for real-time welding work, and a distance between a base material and the welding torch 20. In addition, the sensor unit 150 may include an optical sensor module configured to detect information on welding light within at least a welding work region.

The sensor unit 150 according to an embodiment of the present disclosure may be included in the welding torch 20 and/or the welding information providing device 10 and may sense a welding situation, such as welding temperature, a welding speed, a welding slope, a welding direction, and a distance between a base material and the welding torch 20.

The sensor unit 150 according to an embodiment of the present disclosure may detect at least one of various changes, such as a change in the posture of the worker who grips the welding torch 20, a change in the illuminance of a welding surface, and a change in acceleration of the welding torch 20 and transfer a corresponding electrical signal to the processor 140. That is, the sensor unit 150 may detect a change in state based on the welding torch 20, generate a detection signal accordingly, and transfer the detection signal to the processor 140.

The sensor unit 150 according to an embodiment of the present disclosure may include various sensors, and when the welding torch 20 is driven (or based on worker settings), power may be supplied to at least one preset sensor according to control to detect a change in state of the welding torch 20. In an optional embodiment, the sensor unit 150 may include at least one device among all types of sensing devices that may detect a change in state of the welding torch 20.

For example, the sensor unit 150 may include at least one sensor among various sensing devices, such as an acceleration sensor, a gyro sensor, an illuminance sensor, a proximity sensor, a pressure sensor, a noise sensor, a video sensor, a gravity sensor, etc.

According to the welding system 1 according to an embodiment of the present disclosure, welding light information in the welding work region detected through an illuminance sensor located in a region of the welding torch 20 may be transmitted to the processor 140 through the communication unit 160, and a lighting unit (not shown) and/or the camera unit 110, specifically, the first camera 1101 and/or the second camera 1102, may be controlled based on the welding light information transferred through the illuminance sensor of the welding torch 20.

The acceleration sensor according to an embodiment of the present disclosure may detect movement of the welding torch 20. In detail, the acceleration sensor may measure dynamic force, such as acceleration, vibration, and impact of the welding torch 20 and may measure movement of the welding torch 20.

The gravity sensor according to an embodiment of the present disclosure may detect a direction in which gravity is directed. A detection result of the gravity sensor may be used together with the acceleration sensor to determine the movement of the welding torch 20. In addition, a direction in which the welding torch 20 is gripped may be determined using the gravity sensor. In addition to the aforementioned types of sensors, the welding torch 20 may further include various types of sensors, such as a gyroscope sensor, a geomagnetic sensor, an ultrasonic sensor, and an RF sensor and may detect various changes related to a work environment of welding.

The welding information providing device 10 according to an embodiment of the present disclosure may include an inner cover unit (not referenced) installed in the body 101 and located on a path of the welding video. Through the above structure, foreign substances, such as dust, may be prevented from being introduced into an internal space of the body 101 from the outside.

The embodiments of the present disclosure described above may be implemented in combination with each other.

The above description of the present disclosure is provided for the purpose of illustration, and it would be understood by those skilled in the art that various changes and modifications may be made without changing technical conception and essential features of the present disclosure. Thus, it is clear that the embodiments described above are illustrative and are not restrictive in all aspects. For example, each component described to be of a single type may be implemented in a distributed manner, and likewise, components described to be distributed may be implemented in a combined manner.

The scope of the present disclosure is defined by the following claims, and the meaning and scope of the claims and all changes or modified forms derived from the equivalent concept thereof should be construed as being included in the scope of the present disclosure.

According to an embodiment of the present disclosure, the welding information providing device capable of improving welding accuracy of a worker by illustrating a welding surrounding environment to the worker may be provided.

In addition, according to an embodiment of the present disclosure, the welding information providing device capable of securing an accurate view during welding by preventing foreign substances from penetrating into a space providing welding information may be provided.

In addition, according to an embodiment of the present disclosure, the camera system and a welding information providing device that are free from a ghost phenomenon may be provided.

The effects of the present disclosure are not limited to the effects described above, and should be understood to include all effects that may be inferred from the configuration of the present disclosure described in the detailed description or claims of the present disclosure.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A camera system comprising:

an imaging portion including a camera configured to capture a welding image to acquire a video frame, wherein the camera comprises a front surface configured to receive light emitted from a welding light source, the front surface defining an optical receiving plane of the camera, and wherein a first virtual straight line is defined to be perpendicular to the front surface of the camera; and a light blocking portion located between the camera and the welding light source and including a light blocking cartridge structure configured to control welding light introduced into the imaging portion, wherein the light blocking cartridge structure comprises a first surface facing the front surface of the camera and a second surface opposing the first surface, and wherein a second virtual straight line is defined to be perpendicular to the second surface of the light blocking cartridge structure, the light blocking cartridge structure configured such that the first and second surfaces of the light blocking cartridge structure are tilted relative to the front surface of the camera so that the first virtual straight line and the second virtual straight line intersect each other.

2. The camera system of claim 1, wherein the light blocking cartridge structure includes a liquid crystal panel and an anti-reflective coating layer located on at least one surface of the liquid crystal panel.

3. The camera system of claim 1, wherein the light blocking cartridge structure includes an anti-reflective coating layer having a reflectivity less than 4.0%.

4. The camera system of claim 1, further comprising a cover plate facing the second surface of the light blocking cartridge structure and configured to protect the light blocking cartridge structure, wherein a first distance between the light blocking cartridge structure and the camera is less than a second distance between the light blocking cartridge structure and the cover plate, and wherein the first and second distances are measured when the first and second surfaces of the light blocking cartridge structure are positioned in parallel respectively with the front surface of the camera and the cover plate.

5. The camera system of claim 1, further comprising a controller configured to tilt the first and second surfaces of the light blocking cartridge structure relative to the front surface of the camera such that the first virtual straight line and the second virtual straight line intersect each other.

6. A welding information providing device comprising:
a body provided to cover at least a portion of a worker' face and including a first region facing the worker' face and a second region located in a region opposite to the first region;
an outer cover unit located in the second region of the body;
a camera unit located in the second region of the body and configured to capture a welding video to acquire a video frame, wherein the camera unit includes:
a first camera configured to capture a scene other than welding to acquire a first video frame, and
a second camera configured to capture a welding video to acquire a second video frame,
wherein the second camera comprises a front surface configured to receive light emitted from a welding light source, the front surface defining an optical receiving plane of the second camera, and wherein a first virtual straight line is defined to be perpendicular to the front surface of the second camera;
the outer cover unit further including an outer cover frame and a light blocking cartridge structure located between the outer cover frame and the second camera, wherein the light blocking cartridge structure comprises:
a first surface facing the front surface of the second camera, and
a second surface opposing the first surface and facing the outer cover frame, wherein a second virtual straight line is defined to be perpendicular to the second surface of the light blocking cartridge structure; and
a display unit located in the first region of the body and configured to provide a video generated through the video frame,
the light blocking cartridge structure configured such that the first and second surfaces of the light blocking cartridge structure are tilted relative to the front surface of the camera so that the first virtual straight line and the second virtual straight line intersect each other.

7. The welding information providing device of claim 6, wherein the first camera and the second camera are located on a front portion of the body corresponding to the worker' field of view.

8. The welding information providing device of claim 6, wherein the outer cover unit includes an outer cover plate facing the second surface of the light blocking cartridge structure and configured to protect the light blocking cartridge structure, wherein a first distance between the light blocking cartridge structure and the second camera is less than a second distance between the light blocking cartridge structure and the outer cover plate, and wherein the first and second distances are measured when the first and second surfaces of the light blocking cartridge structure are positioned in parallel respectively with the front surface of the second camera and the outer cover plate.

9. The welding information providing device of claim 6, wherein the light blocking cartridge structure includes a liquid crystal panel and an anti-reflective coating layer located on at least one surface of the liquid crystal panel.

10. The welding information providing device of claim 9, wherein the anti-reflective coating layer includes a first coating layer and a second coating layer formed on opposite surfaces of the liquid crystal panel.

11. The welding information providing device of claim 6, further comprising a controller configured to tilt the first and second surfaces of the light blocking cartridge structure relative to the front surface of the camera such that the first virtual straight line and the second virtual straight line intersect each other.

* * * * *